United States Patent [19]

Oppelt et al.

[11] Patent Number: 5,624,382
[45] Date of Patent: Apr. 29, 1997

[54] METHOD AND APPARATUS FOR ULTRASOUND TISSUE THERAPY

[75] Inventors: Arnulf Oppelt, Spardorf; Helmut Reichenberger, Eckental, both of Germany

[73] Assignee: Siemens Aktiengesellschaft, Munich, Germany

[21] Appl. No.: 302,745

[22] PCT Filed: Feb. 15, 1993

[86] PCT No.: PCT/DE93/00126

§ 371 Date: Sep. 9, 1994

§ 102(e) Date: Sep. 9, 1994

[87] PCT Pub. No.: WO93/17646

PCT Pub. Date: Sep. 16, 1993

[30] Foreign Application Priority Data

May 10, 1992 [DE] Germany ............... 42 07 463.0

[51] Int. Cl.⁶ ...................................... A61B 17/22
[52] U.S. Cl. ..................... 601/2; 601/3; 128/660.03
[58] Field of Search ................. 128/660.03, 736; 601/2–4; 607/97

[56] References Cited

U.S. PATENT DOCUMENTS

| | | |
|---|---|---|
| 4,343,301 | 8/1982 | Indech . |
| 4,601,296 | 7/1986 | Yerushalmi . |
| 4,697,765 | 10/1987 | Wimmer . |
| 4,893,624 | 1/1990 | Lele . |
| 4,938,216 | 7/1990 | Lele . |
| 4,955,365 | 9/1990 | Fry et al. . |
| 5,243,985 | 9/1993 | Aida et al. ............................... 601/4 |

FOREIGN PATENT DOCUMENTS

| | | |
|---|---|---|
| 0170416 | 2/1986 | European Pat. Off. . |
| 0332871 | 9/1989 | European Pat. Off. . |
| 0370890 | 5/1990 | European Pat. Off. . |
| 0459535 | 12/1991 | European Pat. Off. . |
| OS3150513 | 6/1983 | Germany . |
| OS3011322 | 5/1987 | Germany . |
| 2113099 | 8/1983 | United Kingdom . |
| WO89/06512 | 7/1989 | WIPO . |
| WO90/13333 | 11/1990 | WIPO . |

OTHER PUBLICATIONS

"Thermotherapie bei Prostatahyperplasie," Münchener Medizinische Wochenschrift 133, No. 4 (1991), p. 9.
Pyrotech Brochure of EDAP International S.A.

Primary Examiner—Ruth S. Smith
Attorney, Agent, or Firm—Hill, Steadman & Simpson

[57] ABSTRACT

In therapy apparatus for the treatment of tissue in the body of a life form, at least one therapeutic ultrasound transducer emits ultrasound having an effective therapeutic region is provided. The ultrasound intensity in the region of the tissue to be treated is measured. Displacement of the effective therapeutic region and the body of the life form relative to one another ensues on the basis of the measured ultrasound intensity such that at least a part of the tissue to be treated is located in the effective therapeutic region.

44 Claims, 5 Drawing Sheets

METHOD AND APPARATUS FOR ULTRASOUND TISSUE THERAPY

BACKGROUND OF THE INVENTION

1. Field of the Invention

The invention is directed to a therapy apparatus for the treatment of tissue in the body of a life form with ultrasound and is also directed to an operating method for treating benign prostate hyperplasia with such a therapy apparatus.

2. Description of the Prior Art and Related Subject Matter

Therapy apparatus of the type described above are used, for example, for treating benign prostate hyperplasia (BPH= benign enlargement of the prostate due to cell multiplication with progressive constriction of the urethra, increasingly occurring with age in men from about age 50). For therapy of BPH, less invasive methods are being increasingly proposed and investigated as alternatives to the classic method of operation and transurethral resection. For example:

- Hyperthermia of the prostate by heating to 45° C. with microwaves via a rectal applicator (U.S. Pat. No. 4,601,296) or via a urethral applicator (U.S. Pat. No. 4,967,765);
- In a modified form (higher temperature) as thermotherapy in combination with ultrasound imaging and cooling of the urethra (European Application 0 459 535);
- Transrectal irradiation with focused ultrasound and ultrasound imaging (U.S. Pat. No. 4,955,365);
- Non-invasive irradiation with ultrasound using an applicator constructed according to the "crossfire" principle and temperature measurement in the target region;
- Non-invasive irradiation with focused ultrasound with ultrasound imaging (European Application 0 170 416); and
- Laser treatment via a urethra probe (PCT Application WO 90.13333).

In thermotherapy, an over-heating of a larger volume of the prostate with following necrotization is to be effected. The treatment ensues over a time span of minutes through approximately one hour. Due to the irradiation, the tissue in the region to be treated is heated to temperatures above 45° C. through approximately 60° C. and is maintained thereat, so that damage with the goal of a reduction of the multiplied tissue is effected. In the case of hyperthermia, by contrast, a temperature of 45° C. is not exceeded, or is at least not significantly exceeded.

A relatively sharp limitation of the zone of action and an elimination of regions to be generally treated is desired when heating is accomplished with microwaves because of the usually radial, symmetrical emission pattern of microwave antennas with an intensity that slowly decreases with increasing distances from the antenna. In addition to the cooling of the urethra, for example, the employment of radiation-reflective liquids has been proposed (European Application 0 370 890) for this purpose. A continuous monitoring of the resultant heating ensues with temperature probes introduced into the rectum and urethra. Complicated fiber-optical thermometers are thus required in a therapy apparatus working on the basis of microwaves.

Limiting the heating effect to the prostate is unsatisfactory in hyperthermia with transrectal applicators. Thermal damage of tissue outside the prostate can occur.

Like the effect of microwaves, the effect of focused ultrasound is likewise predominantly thermal and leads to necroses having an expanse of approximately 2 mm in diameter and 20 mm in length. A plurality of necroses must be produced side-by-side for a volume treatment. The identification of the target with an ultrasound image only supplies a two-dimensional tomogram with the standard technique. Three-dimensional presentation requires a high outlay for apparatus and time and is not yet clinically available. A complete identification of the position of the therapeutic zone of action of the ultrasound is only possible after a time during which damage will already have occurred.

SUMMARY OF THE INVENTION

An object of the invention is to fashion a therapy apparatus of the type initially cited for tissue therapy, particularly of prostate tissue in BPH conditions, such that it is possible in a simple and optimally exact way to align the body of the patient and the therapeutic region of action of the ultrasound relative to one another such that at least a part of the tissue to be treated is located in the therapeutic region of action of the ultrasound. Insofar as possible, a continuous monitoring of the intensity of the ultrasound should also ensue. Further, the treatment should ensue as non-invasively as possible.

A further object of the invention is to specify an operating method for the therapy apparatus that is especially suitable for the treatment of benign prostate hyperplasia. A specific embodiment of the invention is based on the additional object of fashioning a therapy apparatus of the type initially cited such that a therapeutic region of action of the ultrasound that is tightly spatially limited is achieved.

A limited volume is designationally treated, i.e. damaged, under the influence of ultrasound within the tissue to be treated, specifically the prostate or a prostate lobe, whereby

- sensitive structures such as the urethra in the case of the prostate are protected by cooling and/or
- a measurement and/or monitoring of the ultrasound ensues before and potentially during the therapeutic acoustic-irradiation (insonification) on the basis of at least one miniaturized acoustic pressure sensor (hydrophone) introduced into the tissue, preferably into the urethra in the case of the prostate and the location and/or orientation and/or drive of the source of therapeutic ultrasound is/are varied as warranted after comparison to the values desired at this location.

The treatment ensues over a time span of minutes through approximately one hour. Due to the acoustic-irradiation, the tissue in the target volume is heated to temperatures above 45° C. through approximately 60° C. and is held thereat, so that a damage is effected with the goal of reducing the multiplied tissue. Before the beginning of the actual treatment, the irradiation from each and every transducer is measured by itself, and the combined irradiation from all transducers may be measured as well, with the acoustic sensor or sensors and the arrangement of the transducers is corrected as warranted. A pilot signal having diminished intensity can for this purpose be emitted—as described below—instead of ultrasound having an intensity comparable to that emitted in the therapy. The transducers can be abdominally applied (on the abdominal wall) or can be applied in the rectum and/or perineally (region between scrotum and anus). The position of the target region or the arrangement of the transducers can be additionally checked by ultrasound imaging, whereby the corresponding diagnostic applicators are likewise applied in the aforementioned areas. The acoustic values and the temperature at various points (urethra, rectum) can be monitored during the treatment. This can ensue given therapeutic sound-irradiation (all transducers operating) or can occur as a result of brief-duration operation of only one transducer (brief-duration interruption of the therapy).

Miniaturized acoustic sensors and temperature sensors can be combined in a catheter. Upon introduction into the urethra, the cooling system can thus be connected thereto in a fashion similar to known apparatuses operating on the basis of microwaves. The coolant also assures a good acoustic coupling into the catheter. Miniaturized acoustic sensors or sensor arrays can be constructed based on polymeric piezofoils (for example, polyvinylidene fluoride, abbreviated as PVDF) or piezoceramic (for, example, lead-zirconate-titanate, abbreviated as PZT). Due to the absence of microwave emission, the temperature measurement can ensue economically with solenoids, NTCs or the like.

The limitation of the actively acoustically-irradiated volume can be achieved either with an ultrasound transducer having suitable focusing or by superimposing the acoustic fields of a plurality of transducers. The focus zone (−3 dB zone with respect to the power maximum) of a focusing transducer has a radial diameter $d_{-3dB}=1.22\ c/f \times (F/D)$ and an axial length $Z_{-3dB}=7 \times (F/D)^2$ for harmonic waves, c denoting speed of sound (approximately 1500 m/s in tissue), f denoting the frequency of the emission, D denoting the diameter of the source and F denoting its focal length. For a transducer having D=12 cm, F=8 cm and f=500 kHz, $d_{-3dB}=2.5$ mm and $Z_{-3dB}=9$ mm. When the transducer emits ultrasound with a power density of 0.1 W/cm$^2$, then a power of approximately 60 W/cm$^2$ is present in the focus based on an estimated efficiency of 25% as a consequence of absorption in preceding tissue (fat, muscle) and extrafocal radiation. Leaving non-linear effects out of consideration, approximately 25% thereof is absorbed in the focus zone and converted into heat. A therapeutic effect is achieved within the range of minutes. The effective focus zone in this case is an individual transducer having an oblong shape.

A more compact focus geometry can be achieved by superimposing a plurality of acoustic fields from different directions. Given acoustic-irradiation from approximately orthognal directions, the focus zone can become approximately spherical with three transducers. Possibilities for the sound-irradiation of the prostate are established from the directions of the perineum, lower abdomen (while lying on the back, from laterally/above through the bladder, while bypassing the pubic bone) and the rectum. These directions are approximately orthognal. It is thereby a critical advantage of this arrangement that the aperture of the individual transducer can be relatively small, and disturbing structures (bones, gas volume) in the acoustic path can be evaded. When only one highly focusing transducer with a necessarily larger aperture is employed, an acoustic-irradiation of these structures is difficult to avoid. When an unfocused, planar resonator is employed as an individual transducer, its natural focus has a width $C_{-3dB}=D/3$ at a distance $F=0.75\ d^2 \times f/4c$.

For a transducer having f=875 kHz and D=2.5 cm, $d_{-3dB}=8$ mm and F=7 cm.

Given an output power density of approximately 3 W/cm$^2$, a noticeable heating, but without damage, can be measured in the tissue. When the fields of three of these transducers are superimposed, a spherical focus zone having a diameter of approximately 8 mm is formed. The power absorbed in this volume in the form of heat amounts to approximately 7 W. A therapeutic effect can be expected after a number of minutes.

Dependent on the application location and acoustic path through the target, the transducers can have different apertures, focusing and frequency and can also be differently driven. The combination of a weakly focusing transducer (abdominal or perineal application) with a highly focused transducer (rectal application), thus results in the fact that a volume area can be (pre-)heated to a temperature just below 45° C. and only selected target points are necrotized by the superimposed focus field. It is advantageous that the rectal applicator, which is located close to the prostate, has to have lower power than given exclusive acoustic-irradiation proceeding from the rectum. For example, a transducer having 875 kHz can be combined with a 2 MHz transducer. With diameters and focal lengths of 40 mm each, a −3 dB zone having a diameter of approximately 1 mm and a length of approximately 5 mm derives.

The orientation of the individual transducers relative to the prostate ensues such that the transducers are first coarsely applied to the body surface in the target direction. They are accommodated in a housing having a liquid propagation medium traversed by the ultrasound before emission and a coupling membrane. The transducers are mounted in the housing so as to be pivotable around two planes. Rectally applied transducers are preferably pivotable in one direction and are arranged rotatable around the longitudinal axis of the probe.

While emitting a pilot signal, the transducers are pivoted or rotated until signals are received from the hydrophone or hydrophones lying in the urethra. The signals are optimized by fine adjustment of the direction. Dependent on which region of the prostate is to be acoustically-irradiated, a maximum pressure signal or power signal, left or right −3 dB edge thereof or the like are selected. A higher precision and lack of ambiguity is achieved by employing a plurality of hydrophones distributed along the urethra.

DESCRIPTION OF THE PREFERRED EMBODIMENTS

Figure 1:
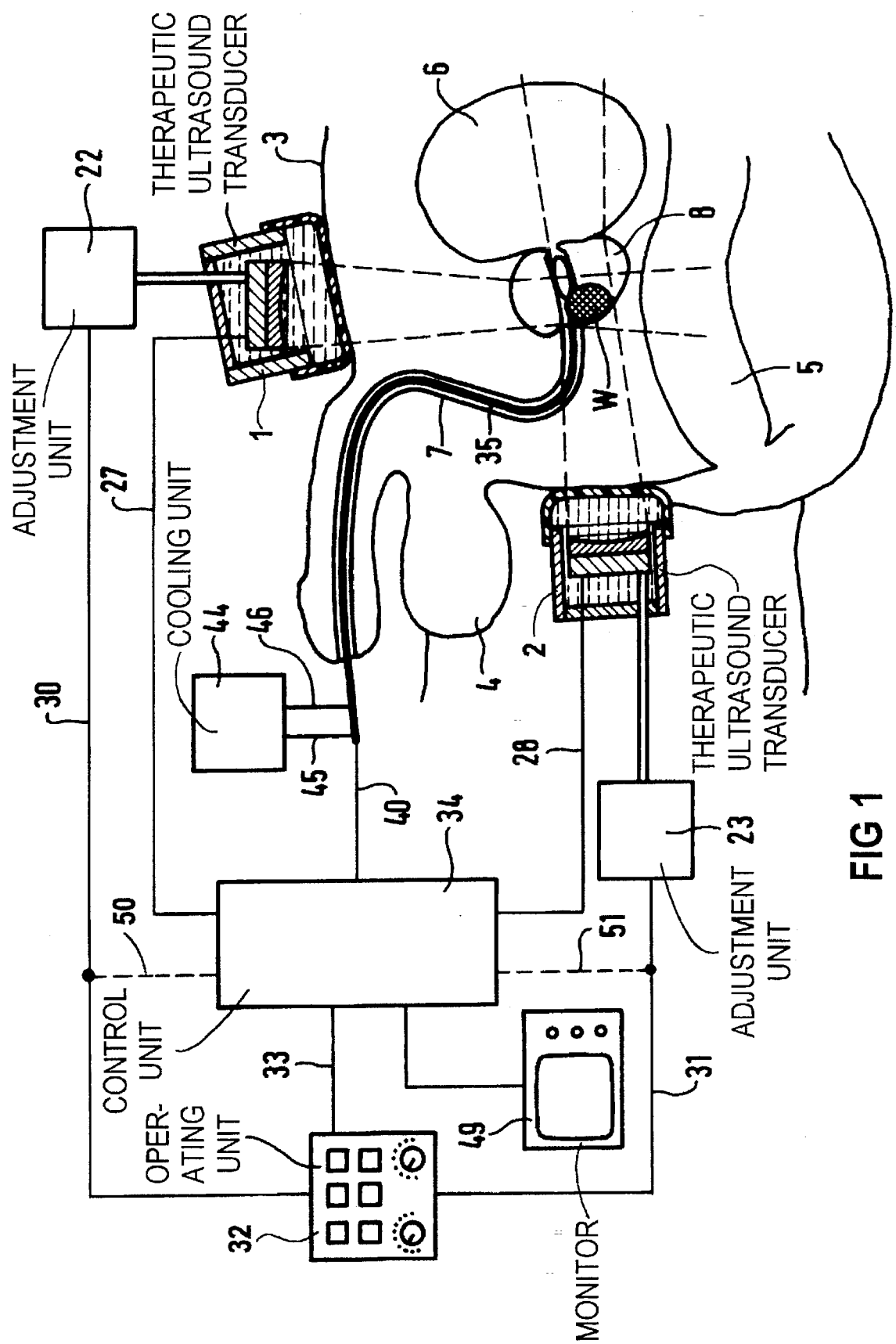
FIG. 1 is a highly schematic longitudinal section through the body of a patient with a therapy apparatus of the invention applied thereto.

The apparatus according to FIG. 1 has two therapeutic ultrasound transducers 1 and 2 that are applied to the body 3 of a patient indicated in cross section in FIG. 1. The application of the ultrasound transducer 1 ensues abdominally in the region of the lower abdomen of the patient lying, for example, on a urological treatment table in a way that is not shown in greater detail. The ultrasound transducer 2 is perineally applied, i.e. between the scrotum 4 and the rectum 5. As may be seen from the "margin rays" of the ultrasound emanating from the ultrasound transducers 1 and 2 shown in dashed lines in FIG. 1, the ultrasound transducers 1 and 2 are respectively aligned to the prostate 8 that precedes the urinary bladder 6 in the region of the opening of the urethra 7 and that surrounds the urethra 7. The prostate 8 exhibits a benign hyperplasia (benign enlargement).

Figure 2:
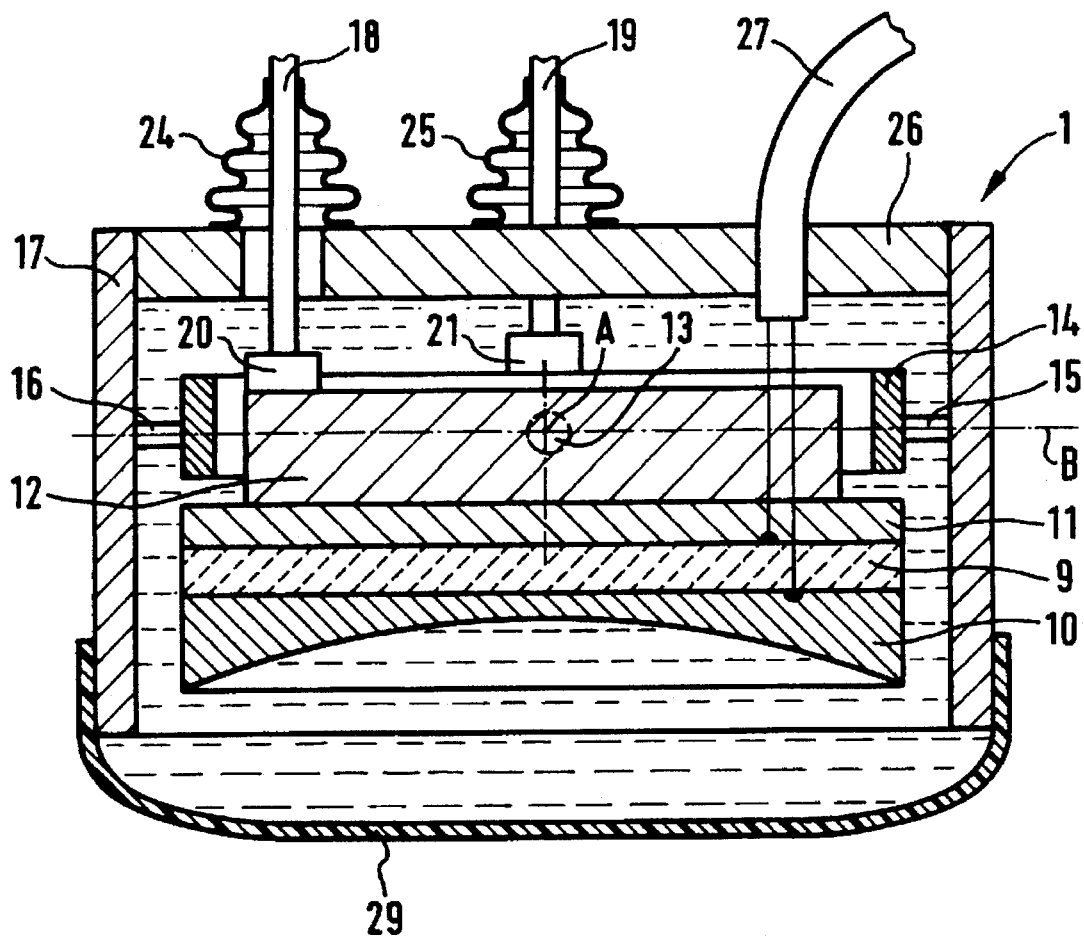
FIG. 2 is a longitudinal section through the ultrasound transducer of the therapy apparatus of FIG. 1 in an enlarged, schematic illustration.

The ultrasound transducers 1 and 2 are constructed as shown in FIG. 2 with reference to the example of the ultrasound transducer 1. In accord therewith, a disc-shaped piezoceramic element 9 is provided as the ultrasound generator. The front side of the piezoceramic element 9 is provided in a known way with a plano-concave, acoustic positive lens 10 that serves the purpose of focusing the generated ultrasound. At its back side, the piezoceramic element 9 is coupled in a known way to a backing 11. The backing 11 is in turn connected to a carrier member 12 shaped like a circular disc that is seated with two pegs—one thereof is indicated in broken lines in FIG. 2 and provided with reference numeral 13—in an intermediate ring 14 pivotable around an axis A residing at a right angle relative to the plane of the drawing. The intermediate ring 14 is in turn seated with two pegs 15 and 16 in a tubular housing 17 pivotable around an axis B that proceeds at a right angle relative to the axis A. In the ultrasound transducer 1 of FIG. 2, the axes A and B intersect.

By means of two rods 18 and 19, the rod 18 being connected by a ball-and-socket joint 20 to the carrier member 12 and the rod 19 being connected by a ball-and-socket joint 21 to the intermediate ring 14, there is the possibility of varying the principal direction of propagation of the generated ultrasound relative to the housing 17 by pivoting around the axis A and/or around the axis B. The rods 18 and 19, which are components in the respective adjustment units 22 and 23 schematically indicated in FIG. 1, are conducted to the exterior of the transducer 1 through a base 26 that closes the housing 17 liquid-tight. A liquid-tight seal around the rods 18 and 19 is provided by respective accordion bellows 24 and 25.

A supply cable 27, via which the piezoceramic element 9 is supplied with a drive voltage in the manner required for generating ultrasound, is likewise conducted liquid-tight through the base 26 in a way that is not shown in greater detail. The supply cable 27 is implemented with two leads, whereby one lead is connected to an electrode (not shown in FIG. 2) provided at the front side of the piezoceramic element 9 and the other lead is connected to an electrode (not shown in FIG. 2) provided at the back side of the piezoceramic element 9. The supply cable 27 and the corresponding supply cable 28 belonging to the ultrasound transducer 2 are only schematically shown in FIG. 1.

The end of the housing 17 facing away from the base 26 is closed liquid-tight with a flexible coupling membrane 29. This serves the purpose of pressing the ultrasound transducer 1 against the body surface of the patient for acoustic coupling. The entire interior of the housing 17 is filled with a liquid acoustic propagation medium for the generated ultrasound. The acoustic propagation medium as well as the material of the coupling membrane 29 preferably exhibit an acoustic impedance that essentially corresponds to that of the body tissue of the patient. Suitable materials, for example, are water and EPDM rubber.

In addition to allowing the swivel motions around the axis A and B—these being executed under motor drive—, the adjustment units 22 and 23 respectively allow a dislocation of each of the ultrasound transducers 1 and 2 in the direction of its center axis upon deformation of the coupling membrane 29. A person skilled in the art is capable of undertaking the measurers required for the realization of the described, motor-driven adjustment motions on the basis of his expertise. In a way not shown in greater detail, the ultrasound transducers 1 and 2 are attached, for example, to carrying devices fashioned like tripods that, leaving the motor-driven adjustment motions that can be effected with the adjustment mechanisms 22 and 23 out of consideration, also allow a manual alignment of the ultrasound transducers 1 and 2 relative to the body 3 of the patient.

The adjustment units 22 and 23 are in communication with an operating unit 32 via respective control lines 30 and 31. This operating unit 32 is provided, among other things, with the operating elements required for executing the described adjustment motions of the adjustment units 22 and 23. The operating unit 32 also includes operating elements with which it is possible to set the intensity of the ultrasound generated by the ultrasound transducers 1 and 2 independently of one another. Data signals corresponding to the selected setting proceed via a line 33 to a control unit 34 that, among other things, contains the electrical generator that generate the alternating voltages that are required in order to be able to drive the ultrasound transducers 1 and 2 to generate ultrasound and which proceed via the supply cable 27 and 28 to the ultrasound transducers 1 and 2.

The ultrasound transducers 1 and 2 are aligned such with the assistance of the adjustment units 22 and 23 that the principal propagation directions of the ultrasound emanating from the ultrasound transducers 1 and 2 are aligned so that the ultrasound emanating from the ultrasound transducers 1 and 2 is superimposed in the region of the prostate 8. The ultrasound emanating from the ultrasound transducers 1 and 2 is only respectively weakly focused. The ultrasound transducers 1 and 2 thus have only a slight degree of focusing that is at least essentially the same in the case of both ultrasound transducers 1 and 2. The focus zones of the ultrasound emanating from the ultrasound transducers 1 and 2 are located in the region of the constriction formed by the respective "margin rays" and at least partially overlap one another. The focus zones have approximately the same dimensions and approximately the same shape. The respective intensities of the ultrasound generated by the ultrasound transducer 1 and by the ultrasound transducer 2 are set such that an intensity adequate for achieving a therapeutic effect can only be achieved within that region wherein the ultrasound generated with the ultrasound transducers 1 and 2 overlaps.

Dependent on whether the treatment ensues as hyperthermia or as thermotherapy, the ultrasound intensities are selected such that a heating of the prostate tissue to a maximum of 45° C. or higher temperatures, preferably 45° C. through approximately 60° C., ensues.

Figure 3:
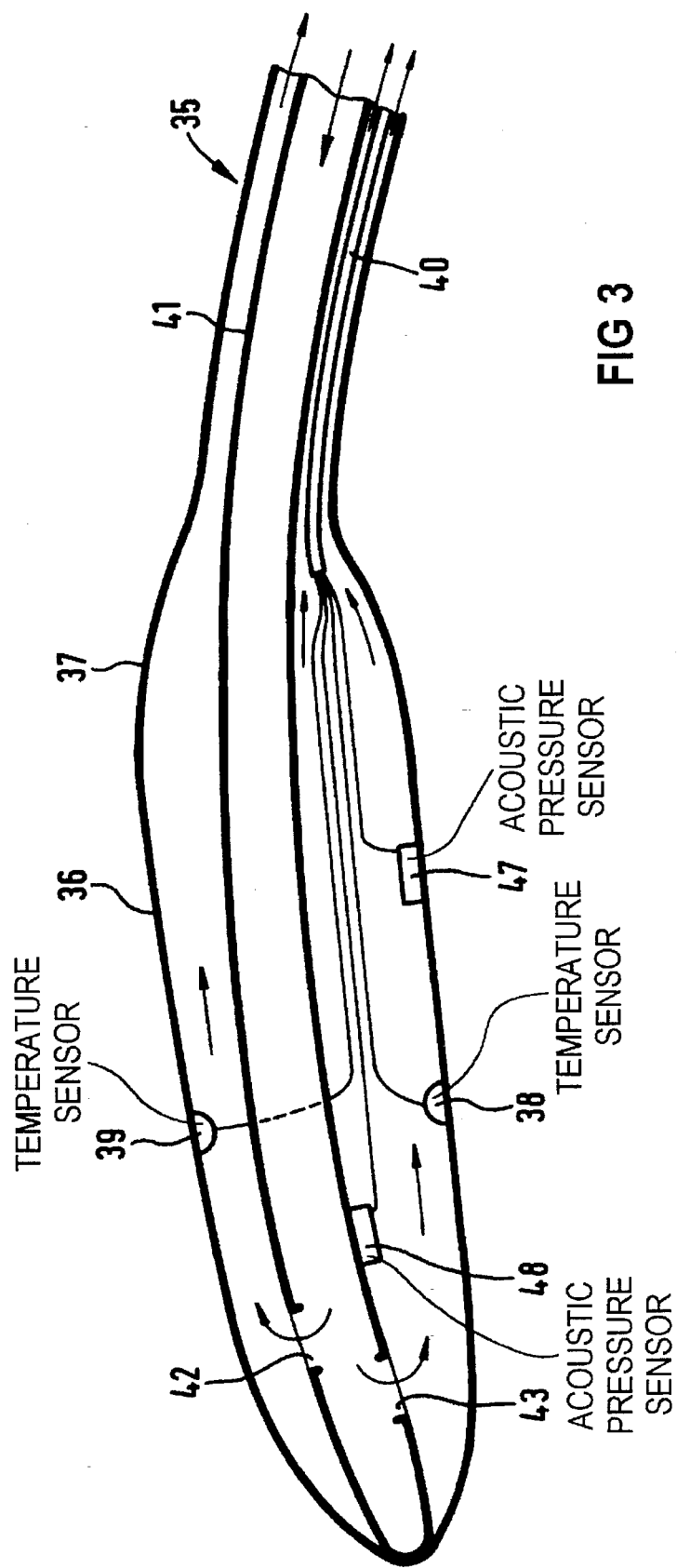
FIG. 3 is a detail of the therapy apparatus according to FIG. 1 in a highly enlarged, schematic illustration and in longitudinal section.

In order, among other things, to be able to monitor the temperatures occurring in the prostate tissue, the therapy apparatus includes a catheter 35 that is introduced into the urethra 7 of the patient to such an extent that the distal end thereof is located in that region of the urethra 7 that is surrounded by the prostate 8. The distal end 36 of the catheter 35 is shown in longitudinal section in FIG. 3. Two temperature sensors 38 and 39, for example NTC resistors, that serve the purpose of measuring temperatures are applied to the inside of a hose-like outside wall 37. The electrical signals corresponding to the measured temperatures proceed via a schematically indicated testing wire 40 to the control unit 34. The multi-lead testing wire 40 is sketched as being a single-lead line in FIG. 1. The catheter 35 is double-channelled, i.e. a hose-shaped inside wall 41 is coaxially arranged inside the outside wall 37. A coolant, for example, water is conveyed inside the inside wall 41 to the distal end 36 of the catheter 35 and passes thereat into the space between the inside wall 41 and the outside wall 37 via flow-through openings 42 and 43 and flows back from the distal end 36 to the proximal end of the catheter 35. The coolant flow is indicated by arrows in FIG. 3. The coolant serves the purpose of protecting the urethra 7 against thermal damage. The coolant flows in a closed circulation loop through a cooling unit 44 schematically indicated in FIG. 1 which is connected via respective lines 45 and 46 to the channel limited by the inside wall 41 and to the channel limited by the inside wall 41 and the outside wall 37. The test wire 40, moreover, proceeds in the channel limited between the inside wall 41 and the outside wall 37.

Two acoustic pressure sensors 47 and 48, preferably in the form of miniaturized hydrophones, are also arranged in the region of the distal end 36 of the catheter 35.

The pressure sensor 47 is applied to the inside of the outside wall 37. The pressure sensor 48 is applied to the outside of the inside wall 41. Other arrangements of the pressure sensors 47 and 48 are possible. The pressure sensors 47 and 48, wherein pre-amplifiers, if necessary can be integrated, are preferably constructed of piezoelectrically activated polymer foil, for example polyvinylidene fluoride (PVDF).

The pressure sensors 47 and 48, which are in good acoustic coupling with the surrounding tissue by means of the medium flowing in the catheter 35, serve the purpose of optimally aligning the ultrasound transducers 1 and 2 with reference to the region of the prostate 8 to be treated. This occurs by first, driving only the ultrasound transducer 1 to output ultrasound, the transducer 1 being aligned with the adjustment unit 22 so that at least one of the pressure sensors 47 or 48 supplies a maximum output signal. The output signals of the pressure sensors 47 and 48, moreover, likewise proceed via the testing wire 40 to the control unit 34 that is connected to a monitor 49 that, among other things, serves the purpose of displaying the pressures measured with the pressure sensors 47 and 48 which are proportional to the intensity of the ultrasound. Subsequently, only the ultrasound transducer 2 instead of the ultrasound transducer 1 is activated to output ultrasound and is likewise aligned with the adjustment means 23 such that at least one of the pressure sensors 47 or 48, preferably the same one as in the case of the ultrasound transducer 1, supplies a maximum output signal. It can then be assumed that the region of maximum intensity of the ultrasound given activation of both ultrasound transducers 1 and 2 is located in the region of the distal end 36 of the catheter 35, particularly in the region of the respective pressure sensor 47 or 48 that delivered the maximum output signal. In order to be certain to avoid damage to healthy tissue, it can be provided that the ultrasound transducers 1 and 2 only output what is referred to as a pilot signal during the described alignment procedure, this being ultrasound having an intensity reduced to such an extent that tissue damage can be reliably precluded.

For implementation of the therapy, both ultrasound transducers 1 and 2 are driven such that an ultrasound intensity which is adequate for heating the tissue to a temperature that is required for achieving a therapeutic effect arises at least in the region of the maximum intensity of the ultrasound. The size of the effective therapeutic region, i.e. of that region wherein the ultrasound intensity is adequate in order to heat the tissue to be treated to the temperature required for achieving a therapeutic effect, can be varied by varying the ultrasound intensity of one or both ultrasound transducers 1 and 2, whereby an increase in the ultrasound intensity produces an enlargement of the effective therapeutic region. In FIG. 1, the effective therapeutic region W is indicated by cross-hatching as an example.

A size of the effective therapeutic region W that corresponds to the respective treatment case can be set by a suitable selection of the ultrasound intensities of the ultrasound generated with the ultrasound transducers 1 and 2. Moreover, the effective therapeutic region W can be varied in position on the basis of a slight adjustment of the ultrasound transducers 1 and 2 relative to one another with the adjustment means 22 and 23, so that the effective therapeutic region W can be displaced little by little when the effective therapeutic region W is smaller than the prostate 8 such that the entire prostate 8, is treated.

The pressure values measured with the pressure sensors 47 and 48 and displayed on the monitor 49 provide information about the current size of the effective therapeutic region W. Additionally, monitoring of the therapy procedure ensues on the basis of the temperature values measured with the temperature sensors 38 and 39, these temperatures values being likewise displayed on the monitor 49. The measured pressure values are also displayed on the monitor 49.

The measured pressure values can also be utilized in order to obtain information about the momentary position of the effective therapeutic region W, by identifying, in the manner described above, the pressure values maximally possible for the ultrasound intensities that have been set and comparing the pressure values arising given an adjustment of the ultrasound transducers 1 and 2 with the adjustment means 22 and 23 to the maximum values. Displacement of the effective therapeutic region into a tissue zone that no longer requires treatment can be recognized from the level of the deviation of the current measured values from the maximum values.

The control unit 34 can compare the measured pressure values to a threshold that is determined dependent on the ultrasound intensities set with the operating unit 32, the upward transgression of which indicates that the effective therapeutic region W has been displaced into the region of healthy tissue. The threshold can be determined by the attending personnel with the assistance of tables or the like, taking the size of the prostate 8 to be treated into consideration, and can be input via the operating unit 32. The control unit 34 may, however, be fashioned such that it automatically calculates the threshold, potentially after entering of the size of the prostate 8 to be treated.

The control unit 34 is expediently fashioned such that it blocks the drive of the ultrasound transducers 1 and 2 when the threshold is downwardly transgressed and only enables a renewed drive of the ultrasound transducers 1 and 2 for generating ultrasound having an ultrasound intensity which is capable of achieving therapeutic effect after a renewed alignment of the ultrasound transducers 1 and 2 in the abovedescribed way.

In addition to the comparison of the pressure values measured with the pressure sensors 47 and 48 to a threshold, the control unit 34 also undertakes a comparison of the temperatures measured with the temperatures sensors 38 and 39 to an upper and to a lower threshold. The thresholds for the temperatures can likewise be entered via the operating unit 32. The upper threshold corresponds to the maximum temperature matched to the respective treatment case; the lower threshold corresponds to the minimum temperature to which the tissue to be treated should be minimally heated selected corresponding to the respective treatment case. When the upper threshold of the temperature is upwardly transgressed, the drive of the ultrasound transducers 1 and 2 is blocked and is not enabled again until the temperature has dropped by a specific amount, for example 5° C. below the upper threshold. When the lower threshold is downwardly transgressed, a corresponding indication is displayed on the monitor 49, informing the attending personnel that a therapeutic effect may no longer be achieved under certain circumstances.

The control unit 34 can also be fashioned such that the adjustment of the ultrasound transducers 1 and 2 with the adjustment units 22 and 23 does not ensue on the basis of a corresponding actuation of the operating unit 32 but is carried out by the control unit 34 upon evaluation of the output signals of the pressure sensors 47 and 48. This is indicated in FIG. 1 in that the control lines 30 and 31 are connected to the control unit 34 via lines 50 and 51 indicated with dashed lines.

The exemplary embodiments set forth below coincide in terms of essential points with that is set forth above, for which reason identical or similar elements carry the same reference characters.

Figure 4:
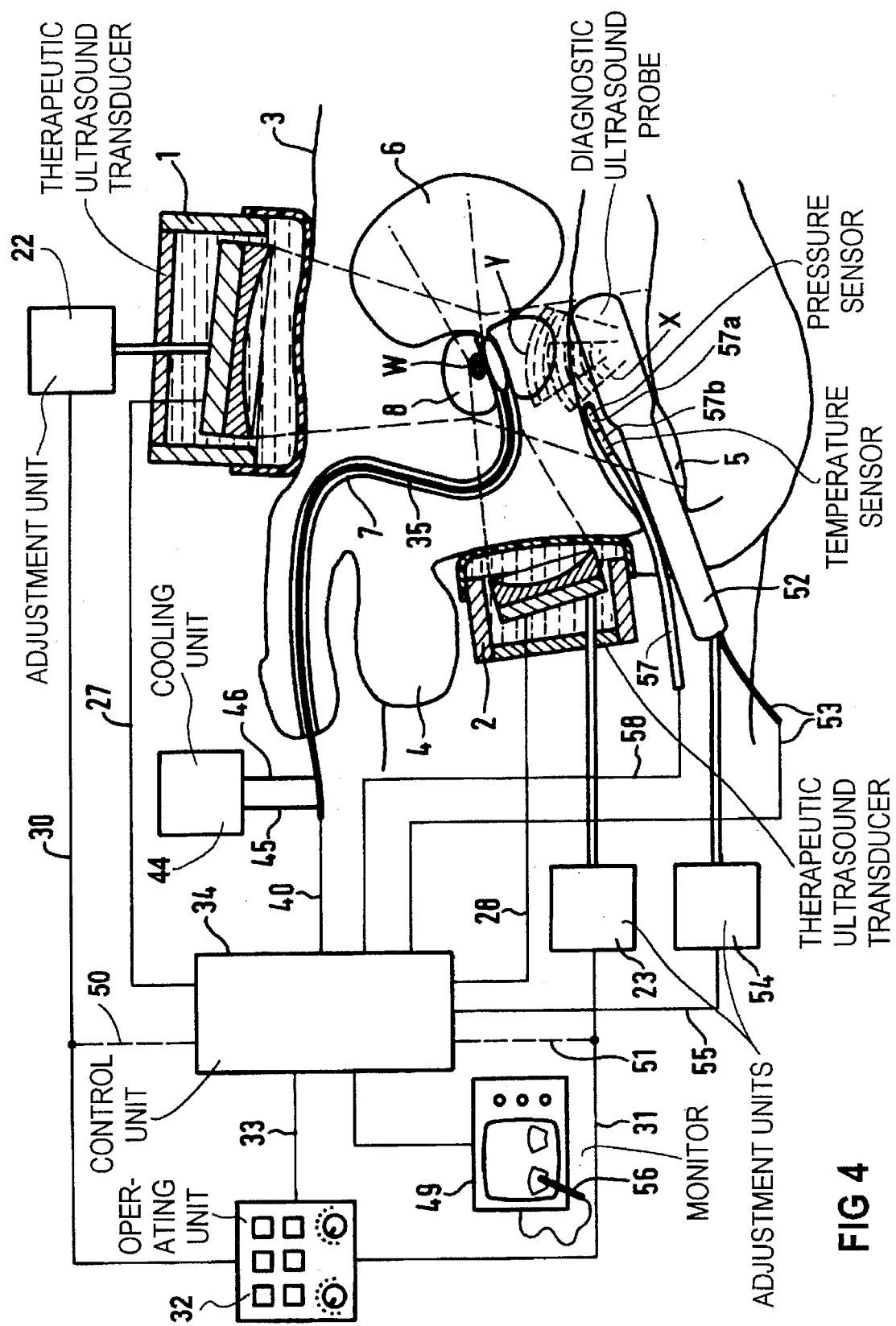
FIGS. 4 and 5 respectively show two further embodiments of therapy apparatus of the invention shown in an illustration analogous to FIG. 1.

Whereas the ultrasound transducers 1 and 2 in the above-described exemplary embodiment only output weakly focused ultrasound and the focus zones in the case of both ultrasound transducers 1 and 2 have essentially the same dimensions, the ultrasound transducers 1 and 2 in the case of FIG. 4 have a different degree of focusing, as indicated by the "margin rays" of the ultrasound emanating from the ultrasound transducers 1 and 2 entered with broken lines. The ultrasound transducer 1 has a lower degree of focusing than the ultrasound transducer 2 and outputs weakly focused ultrasound having a comparatively large focus zone. The ultrasound emanating from the ultrasound transducer 2, by contrast, is highly focused and has a focus zone that is significantly smaller than that of the ultrasound emanating from the ultrasound transducer 2. During the therapy, the ultrasound transducers 1 and 2 are aligned relative to one another such that the focus zone belonging to the ultrasound transducer 2 lies inside the focus zone belonging to the ultrasound transducer 1. After the ultrasound transducers 1 and 2 have been aligned with the adjustment units 22 and 23 on the basis of the output signals of the pressure sensors 47 and 48 before the beginning of the therapy in the way set forth in conjunction with the above-described exemplary embodiment, the displacement of the effective therapeutic zone W, which is extremely small in comparison to the above-described exemplary embodiment, ensues given in exemplary embodiment of FIG. 4 by maintaining the alignment of the ultrasound transducer 1 relative to the body 3, and varying the alignment of the ultrasound transducer 2 with the adjustment unit 23 such that the effective therapeutic zone W scans the regions of the tissue of the prostate 8 to be treated little by little. The smaller focus zone of the ultrasound emanating from the ultrasound transducer 2 thereby always remains within the larger focus zone of the ultrasound emanating from the ultrasound transducer 1; otherwise, a therapeutic effect would not be assured.

As an additional element, the therapy apparatus of FIG. 4 has an ultrasound diagnostics probe 52 suitable for rectal application, this being introduced into the rectum 5 in the way shown in FIG. 4. Ultrasound tomograms of two body slices of the patient, that are preferably shaped like circular sectors and intersect one another, can be produced with the ultrasound diagnostics probe 52. The regions of the sectored body slices that neighbor the ultrasound diagnostics probe 52 are indicated with dashed lines in FIG. 4 and are respectively referenced X and Y. The ultrasound diagnostics probe 52 is placed in the rectum 5 such that the body slices X and Y shown in the ultrasound tomograms proceed through the prostate 8. In a way that is not shown, the ultrasound diagnostics probe 52 contains an ultrasound transducer arrangement suitable for generating the two ultrasound tomograms that is in communication with the control unit 34 via a control and signal line 53. This control unit 34 contains the electronics required for driving the ultrasound transducer arrangement and for processing the signals supplied therefrom and for generating the ultrasound tomograms, this electronics being conventionally fashioned. The two ultrasound sector tomograms are displayed on the monitor 49 in the way indicated in FIG. 4.

The ultrasound diagnostics probe 52, moreover, is attached to a positioning mechanism 54 schematically indicated in FIG. 4 which allows the ultrasound diagnostics probe 52 to be positioned as desired in space within a specific range of adjustment. The positioning mechanism 54 has position transmitters available to it that forward signals corresponding to the spatial position of the ultrasound diagnostics probe 52 to the control unit 34 via a line 55. For example, the positioning mechanism can be fashioned as an articulated arm in a way known from ultrasound technology (compound scan), the articulations thereof having respective angle generators allocated to them. When, thus, the ultrasound diagnostics probe 52 is introduced into the rectum 5 of the patient and is aligned such that a specific region of the prostate 8 to be treated is shown in the two tomograms, the control unit 34 receives signals that represent the position of the body slices X and Y shown in the tomograms.

In a first operating mode that can be selected with the operating unit 32, a mark representing the position of the effective therapeutic region W is mixed into the ultrasound tomograms displayed on the monitor 49. There is then the possibility of aligning the ultrasound transducers 1 and 2 with the adjustment units 22 and 23 such on the basis of a corresponding actuation of the operating unit 32 that the effective region W lies in a specific region of the tissue of the prostate 8 shown in the ultrasound tomograms.

In a second operating mode that can likewise be selected with the operating unit 32, a mark corresponding to the position of the effective therapeutic region W is likewise mixed into the ultrasound tomograms but this mark is independent of the alignment of the ultrasound transducers 1 and 2. The ultrasound diagnostics probe 52 is then positioned such in the rectum 5 that the image of a specific tissue region of the prostate 8 to be treated coincides with the position of the mark corresponding to the effective region W in the two ultrasound tomograms. When this is the case, the control unit 34 drives the adjustment units 22 and 23 in response to a corresponding actuation of the operating unit 32 such that the ultrasound transducers 1 and 2 are aligned such that the effective therapeutic region W of the ultrasound is located in that tissue zone of the prostate 8 whose image coincides with the mark in the ultrasound tomograms.

In a third operating mode selectable with the operating unit 32, there is the possibility of marking a specific tissue region of the prostate 8 in an ultrasound tomogram or in both ultrasound tomograms with a light pen 56, the effective therapeutic region W being displaced to this specific tissue region of the prostate 8 by a corresponding drive of the adjustment units 22 and 23 in response to a corresponding actuation of the operating unit 32.

In the therapy apparatus of FIG. 4, moreover, a measuring probe 57 that contains at least one pressure sensor 57a and at least one temperature sensor 57b in (schematically shown) is introduced into the rectum 5 of the patient in addition to the ultrasound diagnostics probe 52. The measured values acquired with the measuring probe 57 are transmitted to the control unit 34 via a testing wire 58. The corresponding pressure values and temperatures values are displayed on the monitor 49 in addition to the measured values acquired with the catheter 35. A comparison with thresholds in the way set forth in conjunction with the measured values acquired with the catheter 35 can also ensue with respect to the measured values acquired with the measuring probe 57, whereby an upward or downward transgression of the thresholds has the above-described consequences.

Figure 5:
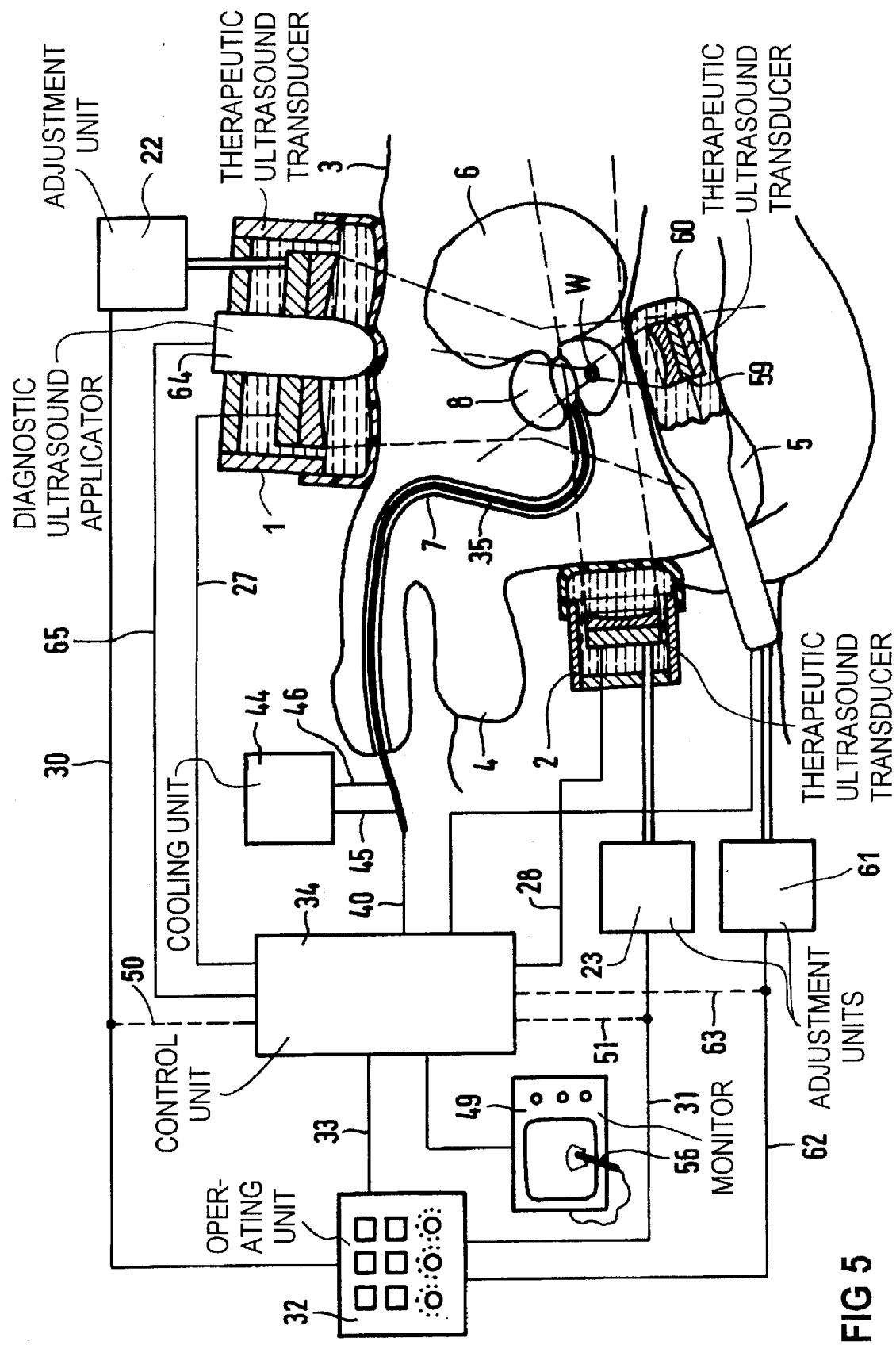

The therapy apparatus of FIG. 5 first differs from that according to FIG. 1 in that an additional therapeutic ultrasound transducer 59 is provided, this being accepted in a probe 60 provided for the rectal application. The ultrasound transducer 59 is mounted—in a way not shown in detail—in the probe 60 (shown partially broken away in FIG. 5) such such that it can be turned around the longitudinal axis of the probe 60 and can be pivoted around an axis that preferably intersects this longitudinal axis at a right angle. An adjustment unit 61, that can be driven by the operating unit 32 via the control line 62 or by the control unit 34 via the line 63, is allocated to the probe 60 and to the ultrasound transducer 59. The probe 60 also has a carrying device (not shown), which for example, is tripod-like.

As in the case of the therapy apparatus of FIG. 1, the ultrasound transducers 1 and 2 are transducers with a low degree of focusing, i.e. they emit only slightly focused ultrasound (see the "margin rays" of the ultrasound emanating from the ultrasound transducers 1 and 2 entered with dashed lines in FIG. 5). By contrast to the therapy apparatus of FIG. 1, the ultrasound intensities, however, are selected such that the superimposition of the ultrasound emanating from the ultrasound transducers 1 and 2 does not yet cause a therapeutic effect. A therapeutic effect that is limited to an extremely small effective therapeutic region W in view of the high degree of focusing of the ultrasound generated with the ultrasound transducer 6 occurs only when a superimposition with the highly focused ultrasound generated with the ultrasound transducer 59 ensues, this ultrasound transducer 59 having a high degree of focusing, as the "margin rays" of the ultrasound emanating from it that are entered with dashed lines shown. The application of the ultrasound transducer 1 again ensues at the lower abdomen of the patient, preferably from the side—in a way that cannot be seen in FIG. 5—, so that the principal propagation directions of the ultrasound emanating from the ultrasound transducers 1, 2 and 59 each reside substantially perpendicularly relative to one another. A region of therapeutic effect W having a nearly spherical shape is achieved in this way.

The alignment of the effective therapeutic region W ensues with reference to the output signals of the catheter 35 in the way set forth in conjunction with the embodiment of FIG. 1; the displacement of the effective therapeutic region W into the region of the tissue of the prostate to be treated preferably ensues in that the ultrasound transducers 1 and 2 retain their respective positions and the ultrasound transducer 59 is adjusted with the adjustment unit 61 such that its focus zone, or the effective therapeutic region W, is positioned in the tissue regions to be treated within that region wherein the ultrasound emanating from the ultrasound transducers 1 and 2 is superimposed.

Additionally, a diagnostic ultrasound applicator 64, with which ultrasound [. . . ] can be generated for producing an ultrasound tomogram of a body slice of the patient containing the effective therapeutic region W, is integrated in the ultrasound transducer 1, that has an enlarged diameter in comparison to FIG. 1. The ultrasound applicator 64, which is accepted in a central bore of the ultrasound transducer 1, is in communication with the control unit 34 via a control and signal line 65. The control unit 34 contains the electronics required for driving the ultrasound transducer contained in the ultrasound applicator 64 and for processing the signals supplied therefrom as well as for generating the ultrasound tomogram. The ultrasound tomogram generated with the assistance of the ultrasound applicator 64 is displayed on the monitor 49.

The ultrasound tomogram can be utilized for monitoring the therapy process. Analogous to the embodiment of FIG. 4, there is also the possibility of undertaking the alignment of the effective therapeutic region W using the ultrasound tomogram.

The invention has been set forth above with reference to the example of treating benign prostate hyperplasia. Other benign or malignant tissue modifications as well as other hyperplasia or tumors, however, can also be treated.

In the exemplary embodiments that have been set forth, the ultrasound transducers each contain a single disc-shaped piezoceramic element. A different structure of the ultrasound transducers is possible. For example, these can contain a mosaic-like arrangement of a plurality of piezoceramic transducer elements.

The focusing of the ultrasound generated with the ultrasound transducer ensues using an acoustic positive lens in the exemplary embodiments that have been set forth. Other types of focusing are possible, for example on the basis of suitable, particularly spherical-concave fashioning or on the basis of electronic measures for focusing (phased array).

The ultrasound transducers contained in the therapy apparatus of the invention need not necessarily be operated with the same frequency. On the contrary, there is the possibility of selecting different frequencies, this being potentially advantageous in conjunction with influencing of the size of the current effective therapeutic region. For the same reason, it can be expedient to drive the individual ultrasound transducers such that the respectively achieved maximum ultrasound intensity is different for the individual ultrasound transducers. In order to create optimum propagation conditions in view of the propagation of the ultrasound emanating from the individual ultrasound transducers and/or in order to prevent damage to healthy tissue, it can be expedient to provide different aperture angles for the individual ultrasound transducers. Thus, for example, it is expedient to provide a relatively small aperture angle for the perennially applied ultrasound transducer 2, whereas a large aperture angle is expedient for the ultrasound transducer 59 placed in the rectum 5 close to the prostate 8.

Although it is usually expedient to provide a plurality of therapeutic ultrasound transducers, the therapy apparatus of the invention can also be realized with a single therapeutic ultrasound transducer.

It can be advantageous under certain circumstances to provide the catheter 35 intended for insertion into the urethra, and potentially the measuring probe 57 placed in the rectum, with more than two pressure and/or temperature sensors. In this case, there is then the possibility within certain limits of measuring the pressure or temperature distribution within a larger tissue region, providing the basis for a more exact control and monitoring of the therapy process.

Although modifications and changes may be suggested by those skilled in the art, it is the intention of the inventors to embody within the patent warranted hereon all changes and modifications as reasonably and properly come within the scope of their contribution to the art.

We claim:

1. Therapy apparatus for the treatment of tissue in the body of a life form, comprising a therapeutic ultrasound transducer that emits therapeutic ultrasound having an effective therapeutic region with an ultrasound intensity therein, means for coupling the ultrasound generated with the ultrasound transducer into the body of the life form, pressure measurement means for obtaining a measurement of pressure present in the region of the tissue to be treated independently of the momentary position of the effective therapeutic region as indicative of the intensity of said therapeutic ultrasound in said region of the tissue to be treated, and means for displacing the effective therapeutic region and the body of the life form relative to one another dependent on the pressure measured by the pressure measurement means for causing at least a part of the tissue to be treated to be located in the effective therapeutic region.

2. Therapy apparatus according to claim 1, wherein said pressure measurement means include at least one hydrophone.

3. Therapy apparatus according to claim 2 further comprising a catheter having a size and shape adapted for introduction into the urethra of the body of the life form, said catheter carrying said hydrophone.

4. Therapy apparatus according to claim 2 further comprising a catheter having a size and shape adapted for rectal introduction into the body of the life form, said catheter carrying said hydrophone.

5. Therapy apparatus according to claim 1 further comprising means for setting the ultrasound intensity present in the effective therapeutic region.

6. Therapy apparatus according to claim 5 further comprising means for measuring the temperature in the region of the tissue including at least one temperature sensor and wherein said means for setting the ultrasound intensity comprise means for setting the ultrasound intensity dependent on the temperature measured by said means for measuring the temperature.

7. Therapy apparatus according to claim 6 wherein said means for setting the ultrasound intensity include means for comparing the temperature measured with the means for measuring the temperature to a reference value and wherein said means for setting the intensity comprise means for setting the intensity dependent on the comparison of said temperature to said reference value.

8. Therapy apparatus according to claim 7 further comprising means for cooling at least a tissue region adjoining the tissue to be treated.

9. Therapy apparatus according to claim 8 wherein said means for setting the setting comprise means for setting the ultrasound intensity in the effective therapeutic region of the ultrasound for bringing the tissue to be treated to a temperature higher than 45° C.

10. Therapy apparatus according to claim 6 further comprising a catheter having a size and shape adapted for introduction into the urethra of the body of the life form, said catheter carrying said temperature sensor.

11. Therapy apparatus according to claim 6 further comprising a catheter having a size and shape adapted for rectal introduction into the body of the life form, said catheter carrying said temperature sensor.

12. Therapy apparatus according to claim 5 wherein said means for setting the ultrasound intensity comprise means for setting the ultrasound intensity dependent on said pressure measured by said pressure measurement means.

13. Therapy apparatus according to claim 12 wherein said means for setting include means for comparing said pressure to a reference value, and for setting said ultrasound intensity dependent on the comparison of said pressure to said reference value.

14. Therapy apparatus according to claim 13 further comprising means for cooling at least a tissue region adjoining the tissue to be treated.

15. Therapy apparatus according to claim 14 wherein said means for setting the intensity comprise means for setting the ultrasound intensity in the effective therapeutic region for bringing the tissue to be treated to a temperature higher than 45° C.

16. Therapy apparatus according to claim 1 further comprising at least one further therapeutic ultrasound transducer, said therapeutic ultrasound transducer and said at least one further therapeutic ultrasound transducer each emitting ultrasound in a principal propagation direction, said therapeutic ultrasound transducers being oriented relative to the body of the life form with their principal propagation directions different from one another and with the ultrasound respectively emanating from said therapeutic ultrasound transducers being superimposed in the region of the tissue to be treated.

17. Therapy apparatus according to claim 16 wherein said ultrasound intensity in said therapeutic region has a first intensity value, and wherein said therapeutic ultrasound transducers emit therapeutic ultrasound respectively at second and third intensity values which are each less than said first value, for producing the first intensity value in said effective therapeutic region by superimposing said ultrasound with the second and third intensity values.

18. Therapy apparatus according to claim 17 wherein said at therapeutic ultrasound transducer comprise in combination means for generating said effective region with a substantially spherical shape due to the superimposition of the ultrasound.

19. Therapy apparatus according to claim 16 wherein said therapeutic ultrasound transducers each comprise an ultrasound transducer emitting ultrasound focused at a focus zone, the respective focus zones of said therapeutic ultrasound transducers lying in the region wherein the ultrasound is superimposed.

20. Therapy apparatus according to claim 19 wherein said therapeutic ultrasound transducers are oriented so that the focus zones at least partially overlap one another.

21. Therapy apparatus according to claim 10 wherein said ultrasound transducers comprise ultrasound transducers having respective focus zones with different dimensions.

22. Therapy apparatus according to claim 19 wherein said therapeutic ultrasound transducers respectively comprise an ultrasound transducer having a smaller focus zone and an ultrasound transducer having a larger focus zone and wherein said means for displacing the effective region and of the body of the life form relative to one another comprise means for displacing the smaller focus zone inside the larger focus zone.

23. Therapy apparatus according to claim 19 wherein said ultrasound transducers comprise ultrasound transducers having respective focus zones with different shapes.

24. Therapy apparatus according to claim 16 wherein said therapeutic ultrasound transducers comprise ultrasound transducers respectively emitting ultrasound at different frequencies.

25. Therapy apparatus according to claim 16 wherein said therapeutic ultrasound transducers comprise ultrasound transducers emitting ultrasound at respective amplitudes which differ in the region of the superimposition of the ultrasound.

26. Therapy apparatus according to claim 16 wherein said therapeutic ultrasound transducers comprise ultrasound transducers respectively having different aperture angles.

27. Therapy apparatus according to claim 16 wherein said therapeutic ultrasound transducers comprise ultrasound transducers respectively different degrees of focusing.

28. Therapy apparatus according to claim 16 comprising means for mounting each of said therapeutic ultrasound transducers to permit pivoting of each therapeutic ultrasound transducer around a respective axis, and wherein said means for displacing comprise means for pivoting each therapeutic ultrasound transducer around its axis with the respective axes intersecting.

29. Therapy apparatus according to claim 28 wherein said means for mounting comprise means for mounting therapeutic ultrasound transducers with their respective axes intersecting at a right angle.

30. Therapy apparatus according to claim 16 further comprising means for driving said ultrasound transducers for emitting a pilot signal from each transducer having an intensity substantially less than the intensity of said therapeutic ultrasound prior to emitting said therapeutic ultrasound, and wherein said means for displacing comprise means for displacing said ultrasound transducers and the body of the life form relative to one another dependent on the intensity of the pilot signal measured by said pressure measurement means.

31. Therapy apparatus according to claim 30 wherein said means for driving comprise means for driving only one ultrasound transducer at a time for emitting the pilot signal.

32. Therapy apparatus according to claim 1 further comprising a probe, containing said therapeutic ultrasound transducer, adapted for rectal application in the body of the life form.

33. Therapy apparatus according to claim 32 wherein said probe has a longitudinal axis, said therapy apparatus further comprising means for mounting said therapeutic ultrasound transducers in said probe to permit rotation around said longitudinal axis and pivoting around a further axis which intersects said longitudinal axis, and wherein said means for displacing comprise means for rotating ultrasound transducer around the longitudinal axis of the probe and for pivoting the ultrasound transducer around said further axis.

34. Therapy apparatus according to claim 33 wherein said means for mounting said ultrasound transducer in said probe comprise means for mounting said ultrasound transducer in said probe with said longitudinal axis of said probe and said further axis intersecting at a right angle.

35. Therapy apparatus according to claim 1, further comprising means for driving said ultrasound transducer for emitting a pilot signal having an intensity substantially less than the intensity of said therapeutic ultrasound prior to emitting said therapeutic ultrasound, and wherein said means for displacing comprise means for displacing said ultrasound transducer and the body of the life form relative to one another dependent on the intensity of the pilot signal measured by said pressure measurement.

36. Therapy apparatus according to claim 1, further comprising an ultrasound diagnostics probe adapted for rectal application in the body of the life form for producing ultrasound tomograms of two body slices of the life form that contain the region of the tissue to be treated; means for displaying said ultrasound tomograms; means interacting with a display of said tomograms on said means for displaying for generating a signal indicating a position in said display, and wherein said means for displacing comprise means for displacing the effective therapeutic region and the body of the life form relative to one another dependent on said signal and on the measurement of pressure obtained by said pressure measurement means.

37. Therapy apparatus according to claim 1 further comprising a diagnostic ultrasound applicator for producing an ultrasound tomogram of a body slice of the life form containing the effective therapeutic region; a housing adapted for application against the body of the life form containing said diagnostic ultrasound applicator and said therapeutic ultrasound transducer; means for displaying said ultrasound tomogram; means interacting with a display of said tomogram on said means for displaying for generating a signal indicating a position in said display, and wherein said means for displacing comprise means for displacing the effective therapeutic region and the body of the life form relative to one another dependent on said signal and on the measurement of pressure obtained by said pressure measurement means.

38. Therapy apparatus according to claim 1 comprising means for cooling at least a tissue region adjoining the tissue to be treated.

39. Therapy apparatus according to claim 1 further comprising means for mounting said therapeutic ultrasound transducer to permit pivoting around an axis, and wherein said means for displacing said ultrasound transducer and the body of the life form relative to one another comprise means for pivoting said ultrasound transducer around said axis.

40. A method for in vivo treatment of benign prostate hyperplasia in the body of a life form, comprising the steps of:

administering therapeutic ultrasound into the body of said life form, said therapeutic ultrasound having an effective therapeutic region, with an ultrasound intensity therein, in the body of said life form;

obtaining a measurement of pressure in a region of the tissue to be treated in the body of the life form independently of a momentary position of the effective region as indicative of the ultrasound intensity of said therapeutic ultrasound in the region of the tissue to be treated in the body of the life form independently of the momentary position of the effective region; and displacing the effective therapeutic region and the body of the life form relative to one another dependent on the measurement of pressure represented by the measured ultrasound intensity for causing at least a part of the tissue to be treated to be located in said effective therapeutic region.

41. A method as claimed in claim 40 wherein the step of administering said therapeutic ultrasound comprises abdominally administering said therapeutic ultrasound.

42. A method as claimed in claim 41 wherein the step of abdominally administering said ultrasound comprises abdominally administering said therapeutic ultrasound from a side of the body of the life form in the region of the lower abdomen of the life form.

43. A method as claimed in claim 40 wherein the step of administering said therapeutic ultrasound comprises perennially administering said therapeutic ultrasound.

44. A method as claimed in claim 40 wherein the step of administering said therapeutic ultrasound comprises rectally administering said therapeutic ultrasound.

* * * * *